United States Patent [19]

Sachs et al.

[11] 4,359,767
[45] Nov. 16, 1982

[54] ULTRASONIC ARRAY

[75] Inventors: Bertram Sachs, Erlangen; Jacques Borburgh, Poxdorf; Ingmar Feigt, Erlangen, all of Fed. Rep. of Germany

[73] Assignee: Siemens Aktiengesellschaft, Berlin & Munich, Fed. Rep. of Germany

[21] Appl. No.: 238,938

[22] Filed: Feb. 27, 1981

[30] Foreign Application Priority Data

Mar. 17, 1980 [DE] Fed. Rep. of Germany ....... 3010210

[51] Int. Cl.³ ............................................... G01S 7/52
[52] U.S. Cl. ..................................... 367/105; 73/626; 367/122
[58] Field of Search ...................... 367/105, 122, 7, 8, 367/138; 73/626

[56] References Cited

U.S. PATENT DOCUMENTS

| | | | |
|---|---|---|---|
| 3,475,551 | 10/1969 | Green et al. | 367/7 X |
| 3,818,426 | 6/1974 | Bonnet et al. | 367/7 |
| 4,075,598 | 2/1978 | Takamizawa et al. | 367/105 X |
| 4,080,838 | 3/1978 | Kuroda et al. | 73/612 |
| 4,119,938 | 10/1978 | Alais | 367/105 X |
| 4,235,111 | 11/1980 | Hassler | 73/626 |

FOREIGN PATENT DOCUMENTS

| | | |
|---|---|---|
| 21534 | 1/1981 | European Pat. Off. . |
| 2443686 | 2/1978 | Fed. Rep. of Germany . |
| 2643918 | 7/1978 | Fed. Rep. of Germany . |
| 592255 | 9/1947 | United Kingdom . |
| 1244551 | 9/1971 | United Kingdom ................... 367/8 |

OTHER PUBLICATIONS

*IBM Technical Disclosure Bulletin*, vol. 22, No. 7, Dec. 1979, pp. 2827-2828, Zumbado, J. A.

"Full Aperture Beamformer Delay Line", *Acoustical Holography*, vol. 5, 1974, pp. 317-333.
Havlice, J. F. et al., "An Electronically Focused Acoustic Imaging Device".
Krautkraemer, "Werkstoffprüfung mit Ultraschall", Third Edition, Springer-Verlag, 1975, pp. 82 and 83, No Translation.

*Primary Examiner*—Richard A. Farley
*Attorney, Agent, or Firm*—Hill, Van Santen, Steadman, Chiara & Simpson

[57] ABSTRACT

In an exemplary embodiment, the transducer elements are arranged in rows and columns, the transducer elements being contacted at both sides by oppositely disposed contact surfaces, and switches being associated with the contacts of the one contact surface as well as with the contacts of the other contact surface for the purpose of adjustment of preselectable transmitting and/or receiving surface of transducer elements during a transmitting/receiving cycle, in particular, for the purpose of dynamic focusing. It is an object of the disclosure to construct an ultrasonic array which can function with an optimally low outlay of switches and which if desired also permits a transition to continuously varied apertures. In accordance with the disclosure, this object is achieved in that transducer elements, with their one contact surface in the direction of the rows, and with their other contact surface in direction of the columns, are contacted together into groups, and that there is maximally associated, with each row group, an individual common row group switch, and that there is maximally associated, with each column group, an individual common column group switch. A transfer to continuously variable aperture is possible in the simplest manner if continuously variable switching elemets, such as controllable resistances, or the like, are utilized as transmitting and/or receiving switches.

13 Claims, 6 Drawing Figures

ULTRASONIC ARRAY

BACKGROUND OF THE INVENTION

The invention relates to an ultrasonic array comprising an arrangement of transducer elements in rows and columns, wherein the transducer elements each have electrical contact means at opposite contact surfaces thereof, and wherein switches associated with the electrical contact means are operable to activate selected ones of the transducer elements to establish preselectable transmitting and/or receiving surfaces during a transmitting/receiving cycle, particularly for the purpose of dynamic focusing.

Ultrasonic arrays having the possibility of switchover for establishing transmitting surfaces and/or receiving surfaces are, for example, known in the case of an individual line array of optically switched transducer elements from the German Pat. No. 24 43 686, and in the case of a multiline-array (with shift register selected columns of transducer elements) from the German Auslegeschrift No. 26 34 918. In such arrays, switches are interposed between the transmit/receive circuitry and one set of contact surfaces while the other set of contact surfaces are connected to a common return path e.g. at ground potential. Also the type of transistor circuit used for switching permits only two states - connection or disconnection of the individual transducer elements in establishing a desired transmitting and/or receiving surface. A continuously variable degree of coupling of the individual elements with the object of producing a continuously variable aperture is not provided; and an introduction of continuously variable switching elements in the prior art systems would lead to an excessively high technical expenditure in view of the number of switches required in such systems.

SUMMARY OF THE INVENTION

It is an object of the present invention to provide an ultrasonic array which requires at the most a considerably reduced number of switches.

In conjunction with the reduced number of switches, it is a further object to be able to change, when desired, to operation with a variable aperture of the transmitting and/or receiving surface, with a minimum technical expenditure.

The object is achieved in accordance with the invention in that first sets of contact surfaces of the transducer elements are connected together to provide for joint switching thereof as respective rows while second sets of contact surfaces are connected together in groups for joint switching as respective columns, there being at the most one switch for each row of transducer elements and one switch for each column of transducer elements.

The invention reduces to a minimum the number of switches required. The technical expenditure on switching and associated control elements is therefore optimally low. This also renders possible the transfer to continuously variable aperture. In an advantageous embodiment of the invention, this transfer is characterized in that row and/or column switches, in particular, however, those switches, which are ground contact switches, are constructed as continuously variable elements; particularly, in the form of controlled resistances which, for the purpose of a continuous establishment of a receiving and/or transmitting surface, render possible a continuous connection of individual transducer elements to the surface, so that, in this manner, a continuously variable aperture results. A controllable field effect transistor or controllable diodes, or the like, can serve as a continuously controllable resistance element. The continuously varied aperture ensures that, for every examination depth, the near-far field boundary can be optimally utilized for the desired applied purpose. An erratic switching over to individual depths is no longer present. The continuously varied aperture; in particular, the continuously growing aperture, such as always results in the receiving mode, in addition, always leads to a sound pressure distribution in the manner of a center alignment; in particular, a Gaussian profile. Such a sound pressure distribution, however, optimally suppresses acoustic minor (or side) lobes; an interfering influence of acoustic minor lobes in particular on the lateral resolution, is hardly present any longer (see Krautkrämer "Werkstoffprüffung mit Ultraschall", [translation of title: Material Testing with Ultrasound], 3rd edition, Springer-Publishing House 1975, pages 82 and 83).

Further advantages of the invention shall be apparent from the subclaims. An embodiment of the ultrasonic array corresponding to the subclaims 10-13 is here also particularly of significance; an additional contact coating, connected to ground, shielding (or screening) high frequency, prevents with certainty electromagnetic radiation in the case of an open ground switch; i.e., in the case of absence of a ground connection.

The invention shall be explained in greater detail in the following on the basis of exemplary embodiments in conjunction with the accompanying drawing sheet; and other objects, features and advantages will be apparent from this detailed disclosure and from the appended claims.

DETAILED DESCRIPTION

Figure 1:
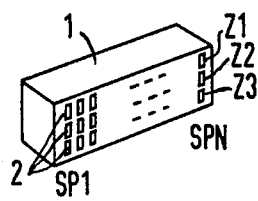
FIG. 1 is a diagrammatic perspective view illustrating the basic construction of a multirow-array.

In FIG. 1, the array carrier member 1 exhibits ultrasonic transducer elements 2 at its application surface. The transducer elements are here arranged in columns SP1 through SPN and in rows Z1, Z2, and Z3. The number of rows in the present instance is equal to three. The number of columns is very much greater; it lies, for example, in the range from about eighty to about one hundred and twenty.

Figure 2:
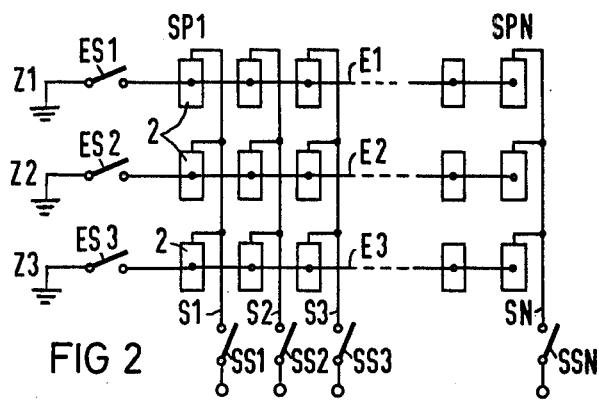
FIG. 2 illustrates a first embodiment in a basic circuit diagram.

FIG. 2 illustrates the first embodiment of a groupwise contacting of transducer elements along the columns and the rows. The transducer element contact layers for the bank of column conductor paths S1 through SN are disposed, respectively, on the rear side of the respective transducer elements 2. The column switches for the column conductor paths S1 through SN are referenced with SS1 through SSN. The row conductor paths are, respectively, indicated with E1 through E3 and form a matrix with the column conductor paths S1 through SN. The contacting of the transducer elements along the rows proceeds, as indicated, on the front side. The row switches are referenced with ES1 through ES3. In the present instance the row switches are ground potential switches. Correspondingly, the column switches SS1 through SSN are the hot (non-ground potential) switches for the transmitting energy in the transmitting mode, or for the received energy in the receiving mode. The method of operation of the basic circuit diagram of FIG. 2 thus is such that, for the purpose of transmission, a preselectable number of column switches; for example SS1 through SS3, is closed at the commencement of every scanning, together with the three row switches ES1 through ES2. Subsequent to emission of a transmit pulse by the transmitting surface (in the present instance, for example, formed from six individual switch elements SS1–SS3 and ES1–ES3), e.g. the two row switches ES1 and ES3 are again opened for the two exterior rows Z1 and Z3. In the case of a closed switch ES2 and closed switches SS1 through SS3, thus first the three elements of the center row Z2 receive echo signals; the switches ES1 and ES3 of the exterior rows ae only closed delayed by a specific period and thus are switched over, somewhat delayed, to provide a larger receiving surface. In this manner, dynamic focusing for the receiving mode results.

The described operation is now repeated successively with progressive forward clock pulsing of the ultrasonic beam in the direction of the rows. This proceeds in the conventional manner in that, following every transmitting/receiving cycle, for the following transmitting/receiving cycle, the transmitting/receiving block is forward clock pulsed by one column through closing of a following column switch, with a simultaneous opening of the respectively first column switch of this block.

However, the described circuit is merely exemplary. Modifications are possible in every respect. Thus, for example, it can also be ensured in the transmitting mode that individual switches of a block are closed at different times. As a consequence of this, dynamic focusing in the transmitting mode is already possible. The column switches SS1 through SSN, as well as also the row switches ES1 through ES3, can be normal transistor switches such as are customarily employed in array technology. However, it is of advantage if at least a portion of the switches is replaced by continuously variable switching elements. The possibility hereby results of the transfer to continuously variable aperture. The focus adaptation (or matching) thus proceeds dynamically without steps (or jumps); the acoustic pressure distribution hereby resulting optimally suppresses acoustic side (or minor) lobes. A preferred embodiment with continuously variable switching elements is illustrated, for example, in FIG. 4. Here, specifically for dynamic focusing in the receiving mode, the row switches ES1 through ES3 (ground switches) are replaced by continuously controllable resistances 3 through 5. The controlled resistance elements can be controllable field effect transistors or controllable diodes, or the like.

Figure 3:
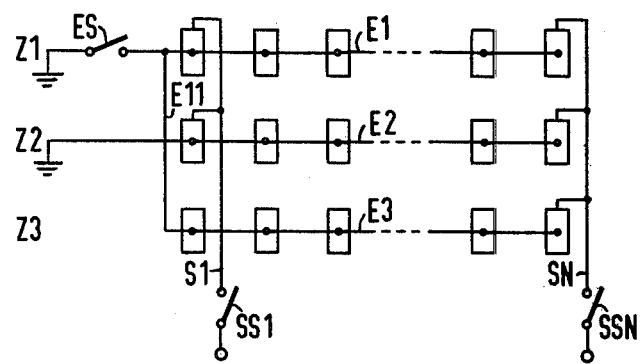
FIG. 3 illustrates a second embodiment in a basic circuit diagram.

The basic circuit diagram of FIG. 3 illustrates a further simplification of the circuit diagram of FIG. 2 to the extent that the two exterior rows Z1 and Z3 are transversely connected via a transverse contacting E11. The center line Z2 is connected directly to ground potential. Due to the transverse contacting E11, only a single row switch ES is still necessary for the two exterior rows. Also this row switch ES, in a special embodiment, e.g., according to FIG. 5, can again be replaced by a continuously controllable resistance element 6.

Figure 4:
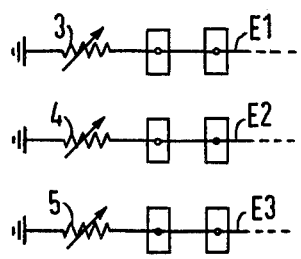
FIGS. 4 and 5 illustrate modifications of the basic circuit diagram of FIGS. 2 and 3 through the introduction of continuously variable ground switches.
Figure 5:
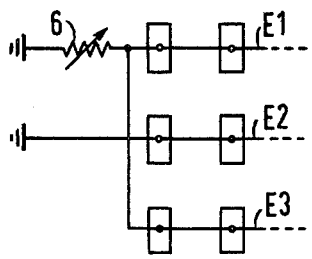
Figure 6:
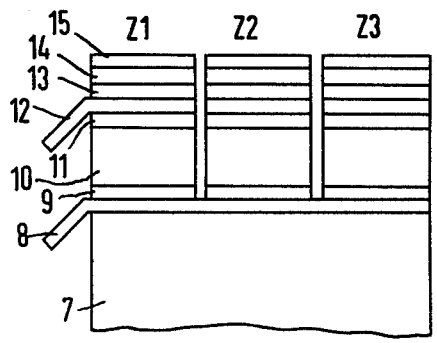
FIG. 6 illustrates the layer construction of an ultrasonic array according to the invention.

FIG. 6, finally, illustrates the layer construction of an ultrasonic array with electrical contacting corresponding to FIG. 2, or 4, respectively, (or also FIG. 3, or 5, respectively, in the case of corresponding transverse contacting). Thus, according to the illustration in FIG. 6, following an attenuation member 7 is a layer such as 8 providing column electrical contact means arranged in columns which serve as column conductor paths S1 through SN and which can be connected to the column switches SS1 through SSN, respectively. In the next layer arrangement, there then follow the transducer elements formed from piezo-element layer 10 with rear-side and front-side contacting layers 9, and 11, respectively. In an additional layer 12, there then follow, arranged in rows, row electrical contact means which provide row conductor paths E1 through E3 (switching ground) and to which the row switches ES1 through ES3, or 3, 4, 5 (or, in the case of corresponding transverse contacting, ES, or 6, respectively) can be connected. Finally, there then follow, in a further layer arrangement along the rows, via adaptation layers 13, layers 14 for a shielding ground against high frequency (HF) interference, and thereupon again layers 15 for application-side insulation.

All the illustrated embodiments have merely an exemplary character; various modifications are possible; e.g., also to the effect that randomly varying numbers of rows and columns are selected. The array, can for example, also possess a square form; namely, when the number of rows is equal to the number of columns. The size of the individual transmitting and/or receiving surfaces to be connected can be widely varied (e.g. also according to program) selected through correspondingly varying activation (or selection) of individual column and row switches. The division (distribution) can also be such that, along the columns and/or also the rows, always any desired number of transducer elements is respectively electrically contacted together into groups, so that thus, also within the columns and/or rows, any desired group activations (or selections) are possible via correspondingly associated group switches. All these indicated circuit variations are intended to fall within the scope of the invention.

It will be apparent that many modifications and variations may be effected without departing from the scope of the novel concepts and teachings of the present invention.

We claim:

1. An ultrasonic array comprising an arrangement of transducer elements in rows and columns, said transducer elements having opposite contact surfaces at opposite sides thereof, electrical contact means in electrical contact with said opposite contact surfaces of said transducer elements, and switch means being associated with the electrical contact means and being operative for forming preselectable transducing surfaces from the transducer elements during a transducing cycle, in particular for the purpose of dynamic focusing, said contact surfaces of said transducer elements (2) comprising row-connecting contact surfaces and column-connecting surfaces, said electrical contact means comprising row contact means for connecting the row-connecting contact surfaces in a direction along the rows (Z1 through Z3) and comprising column contact means for connecting the column-connecting contact surfaces in a direction along the columns (SP1 through SPN) to define respective row and column groups of transducer elements, said switch means comprising at least one row group switch (ES1 through ES3, or ES, respectively) for controlling activation of at least one row group, and comprising column group switches (SS1 through SSN) for controlling activation of the column groups, transverse contacting means (E11) electrically connecting respective contact means of a plurality of groups, and said switch means comprising an individual switch (ES) for actuation to control joint activation of the contact means (E1, E3), of said plurality of groups.

2. An ultrasonic array according to claim 1, with said switch means comprising hot switch means for controlling application of an electrical potential other than ground potential, and comprising ground switch means for controlling application of ground potential, one of the row contact means and the column contact means having said hot switch means for controlling application thereto of a potential different from ground potential, and the other of the row contact means and the column contact means having said ground switch means for controlling application thereto of ground potential.

3. An ultrasonic array according to claim 2, with the number of one of said row groups and column groups being smaller than the other, said ground switch means being associated with the one of said row groups and column groups which is smaller in number, and said hot switch means being associated with the other of said row groups and column groups which is larger in number.

4. An ultrasonic array according to claim 3, with said arrangement having a number of column groups (SP1 through SPN) which is considerably greater than the number of row groups, the column groups (SS1 through SSN) having the hot switch means, and the row groups having the ground switch means (ES1 through ES3, or ES, respectively).

5. An ultrasonic array according to claim 4, with at least one of said row groups having an individual ground switch means (ES1 through ES3 or ES) associated therewith.

6. An ultrasonic array according to claim 5, with at least one of said row groups (Z2) being directly connected with ground potential, and other of said row groups (Z1 and Z3) being transversely connected and having the individual ground switch means (ES) in common for controlling activation of said other of said row groups jointly.

7. An ultrasonic array according to claim 1, with said row group and column group switches being transistor switches.

8. An ultrasonic array comprising an arrangement of transducer elements in rows and columns, said transducer elements having opposite contact surfaces at opposite sides thereof, electrical contact means in electrical contact with said opposite contact surfaces of said transducer elements, and switch means being associated with the electrical contact means and being operative for forming preselectable transducing surfaces from the transducer elements during a transducing cycle, in particular for the purpose of dynamic focusing, said contact surfaces of said transducer elements (2) comprising row-connecting contact surfaces and column-connecting surfaces, said electrical contact means comprising row contact means for connecting the row-connecting contact surfaces in a direction along the rows (Z1 through Z3) and comprising column contact means for connecting the column-connecting contact surfaces in a direction along the columns (SP1 through SPN) to define respective row and column groups of transducer elements, said switch means comprising at least one row group switch (ES1 through ES3, or ES, respectively) for controlling activation of at least one row group, and comprising column group switches (SS1 through SSN) for controlling activation of the column groups, said row group and column group switches including ground potential switches (ES1 through ES3, or ES respectively) comprising continuously variable elements (3 through 5) connected between ground potential and the associated row contact means for providing continuously variable control of the excitation of such associated row contact means, thereby to provide a continuously variable control of the connection of individual transducer elements (2) in a transducer surface, so that, in this manner, a continuously variable aperture results.

9. An ultrasonic array according to claim 8, with said continuously variable elements each comprising a controllable solid state semiconductor device which is operable to provide a continuously variable controllable resistance.

10. An ultrasonic array comprising an arrangement of transducer elements in rows and columns, said transducer elements having opposite contact surfaces at opposite sides thereof, electrical contact means in electrical contact with said opposite contact surfaces of said transducer elements and switch means being associated with the electrical contact means and being operative for forming preselectable transducing surfaces from the transducer elements during a transducing cycle, in particular for the purpose of dynamic focusing said contact surfaces of said transducer elements (2) comprising row-connecting contact surfaces and column-connecting surfaces, said electrical contact means comprising row contact means for connecting the row-connecting contact surfaces in a direction along the rows (Z1 through Z3) and comprising column contact means for connecting the column-connecting contact surfaces in a direction along the columns (SP1 through SPN) to define respective row and column groups of transducer elements, said switch means comprising at least one row group switch ES1 through ES3, or ES, respectively) for controlling activation of at least one row group, and comprising column group switches (SS1 through SSN) for controlling activation of the column groups, said switch means comprising group potential switch means for controlling application of ground potential, said arrangement of transducer elements having said group potential switch means controlling activation of at least one of said row and column groups, and further having a capacitively coupled high frequency shielding layer (14) which is constantly connected to ground potential.

11. An ultrasonic array according to claim 10, with said arrangement having a layer construction with the electrical contact means comprising row and column contact layers (12, 8), and said shielding layer (14) overlying one of said contact layers, an adaptation layer (13) being interposed between said one of said contact layers and said shielding layer.

12. An ultrasonic array according to claim 10, with an additional insulating coating (15) overlying the shielding layer (14) at an application side of the arrangement.

13. An ultrasonic array according to claim 10, with said arrangement having a layer construction comprising an attenuation member (7), and successively in front of the attenuation member:
- (a) a column layer (8) providing each of said column contact means (S1 through SN) and to which the column group switches (SS1 through SSN) can be connected;
- (b) a piezo-element layer (10) providing the transducerelements, said piezo-element layer having rear-side and front-side contacting layers (9, 11);
- (c) a row layer providing each of said row contact means (E1 through E3) and to which the row group switches (ground switches ES1 through ES3) can be connected;
- (d) an adaptation layer (13), a grounded shielding layer (14) for the shielding against high frequency interference, and a further layer (15) for providing application-side insulation.

* * * * *